(12) United States Patent
Lim et al.

(10) Patent No.: US 12,172,028 B2
(45) Date of Patent: Dec. 24, 2024

(54) LIGHT OUTPUTTING DEVICE FOR SCALP CARE

(71) Applicant: LG ELECTRONICS INC., Seoul (KR)

(72) Inventors: Gueisam Lim, Seoul (KR); Sungho Hong, Seoul (KR); Sangwon Kim, Seoul (KR); Haeseok Eo, Seoul (KR); Dongwon Kim, Seoul (KR); Saejung Kim, Seoul (KR); Yongju Yang, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 730 days.

(21) Appl. No.: 17/285,740

(22) PCT Filed: May 29, 2019

(86) PCT No.: PCT/KR2019/006445
§ 371 (c)(1),
(2) Date: Apr. 15, 2021

(87) PCT Pub. No.: WO2020/080636
PCT Pub. Date: Apr. 23, 2020

(65) Prior Publication Data
US 2022/0001195 A1    Jan. 6, 2022

Related U.S. Application Data
(60) Provisional application No. 62/746,566, filed on Oct. 17, 2018.

(30) Foreign Application Priority Data
Apr. 23, 2019    (KR) .......................... 10-2019-0047475

(51) Int. Cl.
    *A61N 5/06*    (2006.01)
    *A61N 5/067*    (2006.01)
    *F21V 8/00*    (2006.01)

(52) U.S. Cl.
    CPC ........... *A61N 5/0616* (2013.01); *A61N 5/067* (2021.08); *G02B 6/0006* (2013.01); *G02B 6/001* (2013.01);
    (Continued)

(58) Field of Classification Search
    CPC .................. A61N 5/0616; A61N 5/067; A61N 2005/063; A61N 2005/0647;
    (Continued)

(56) References Cited

U.S. PATENT DOCUMENTS

| | | | |
|---|---|---|---|
| 2002/0128696 A1* | 9/2002 | Pearl | A61N 5/0617 606/9 |
| 2014/0276248 A1* | 9/2014 | Hall | A61N 1/0432 604/20 |

FOREIGN PATENT DOCUMENTS

| | | | |
|---|---|---|---|
| CN | 204765912 U | * | 11/2015 |
| KR | 10-2004-0012937 A | | 2/2004 |

(Continued)

*Primary Examiner* — Carl H Layno
*Assistant Examiner* — Aya Ziad Bakkar
(74) *Attorney, Agent, or Firm* — Birch, Stewart, Kolasch & Birch, LLP

(57) ABSTRACT

According to an embodiment of the present disclosure, a light outputting device for scalp care includes a dome-shaped outer case defining an appearance, an inner case formed inside the outer case, and a plurality of light sources disposed in a space between the outer case and the inner case, wherein the plurality of light sources include a plurality of first laser light sources, and the optical outputting device includes a plurality of light guide mechanisms arranged corresponding to the plurality of first laser light (Continued)

sources to distribute laser light emitted from the first laser light sources apply the laser light toward the inner case.

18 Claims, 10 Drawing Sheets

(52) U.S. Cl.
CPC *A61N 2005/063* (2013.01); *A61N 2005/0647* (2013.01); *A61N 2005/0652* (2013.01); *A61N 2005/0665* (2013.01)

(58) Field of Classification Search
CPC .... A61N 2005/0652; A61N 2005/0665; G02B 6/0006; G02B 6/001
See application file for complete search history.

(56) References Cited

FOREIGN PATENT DOCUMENTS

| KR | 10-2011-0113970 | A | | 10/2011 |
|----|----|----|----|----|
| KR | 10-2014-0057796 | A | | 5/2014 |
| KR | 20140057796 | A | * | 5/2014 |
| KR | 10-2015-0101709 | A | | 9/2015 |
| KR | 20150101709 | A | * | 9/2015 |
| KR | 10-1832903 | B1 | | 2/2018 |

* cited by examiner

[Figure 1]
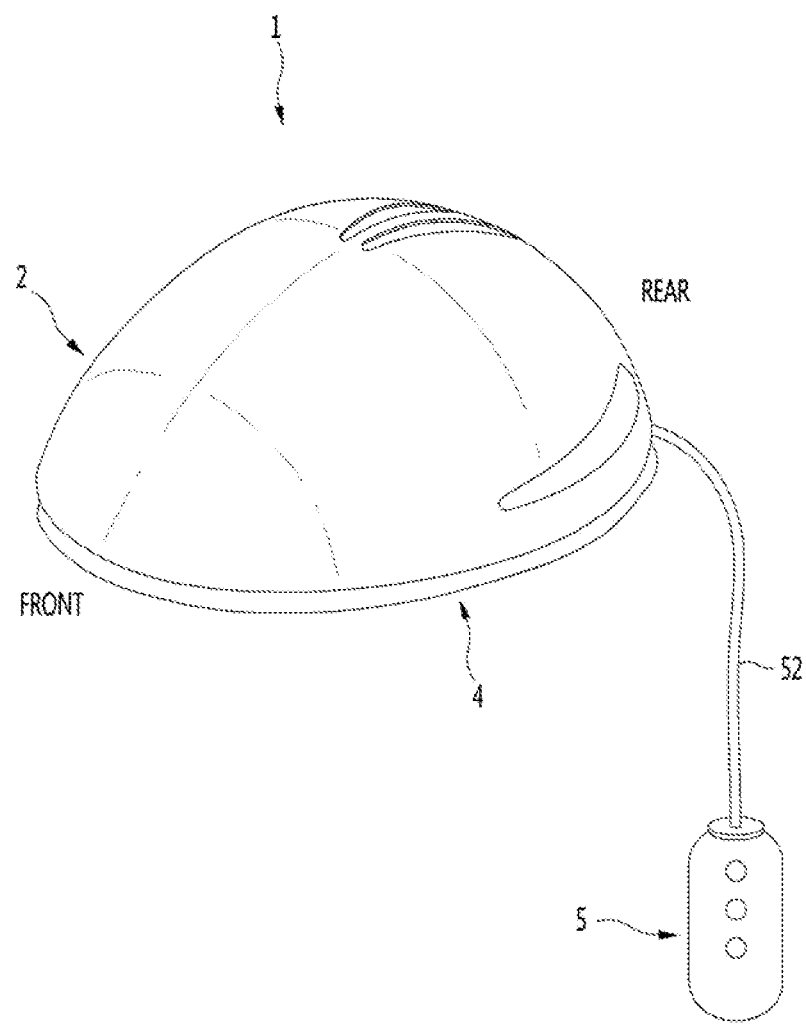

[Figure 2]
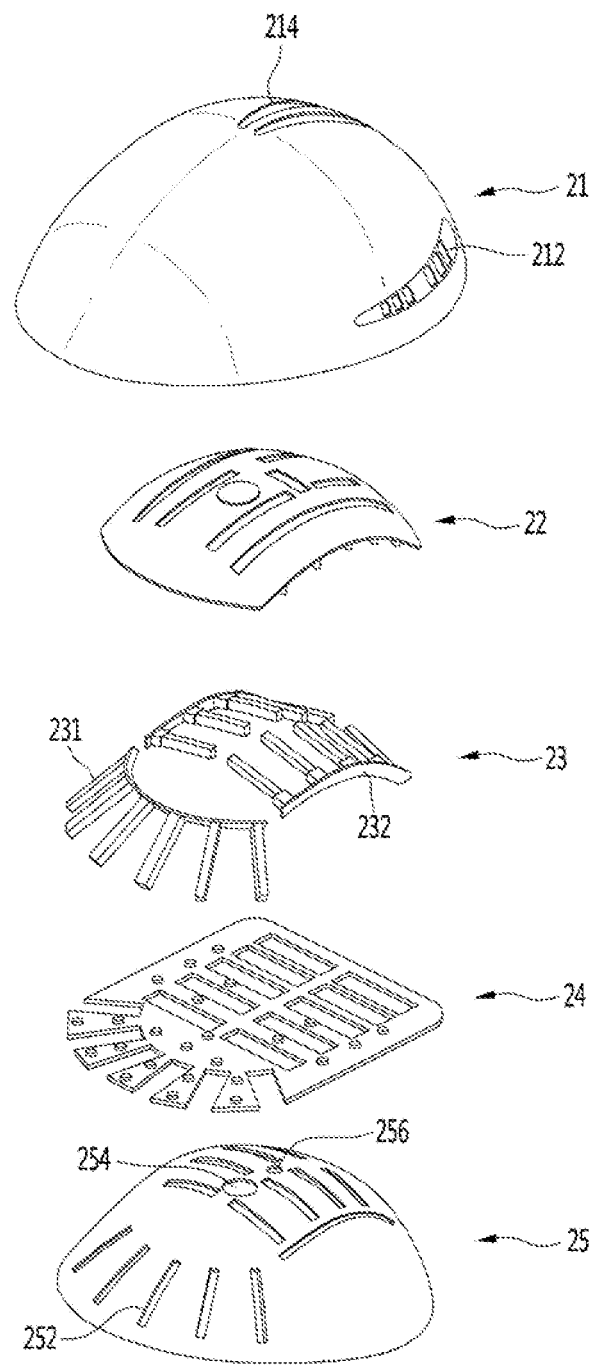

【Figure 3】
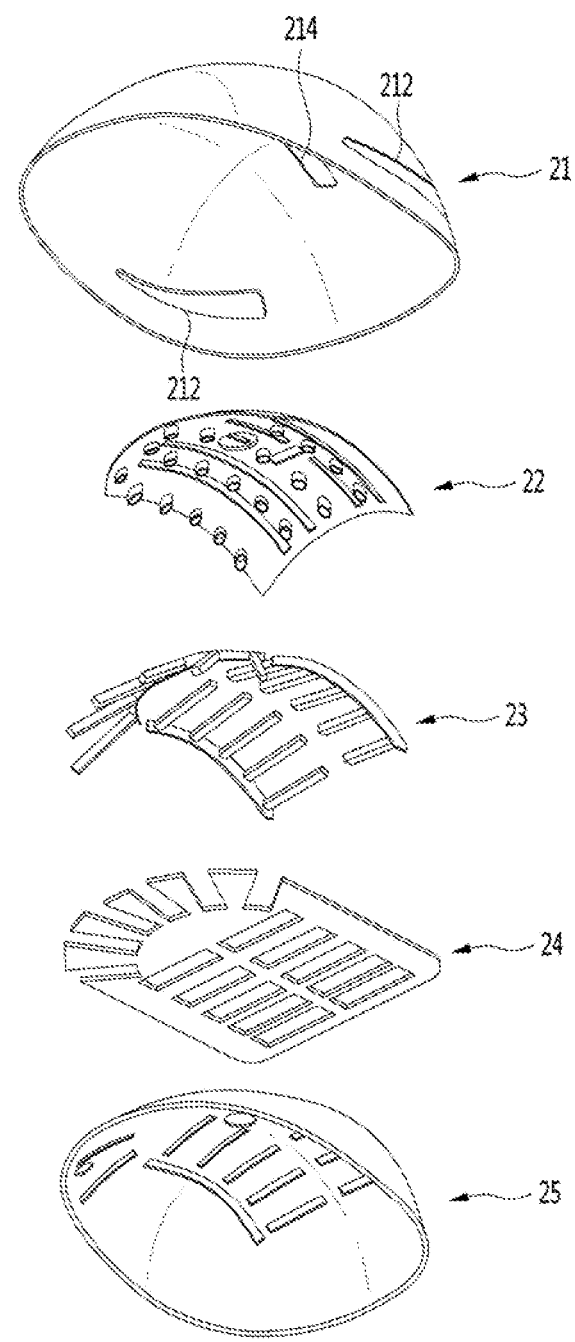

[Figure 4]
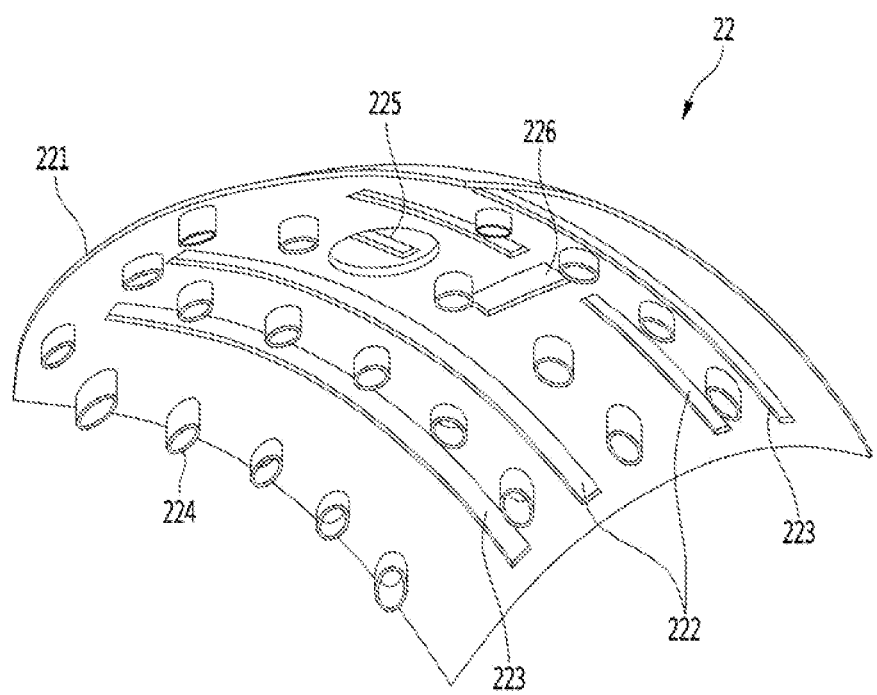

[Figure 5]
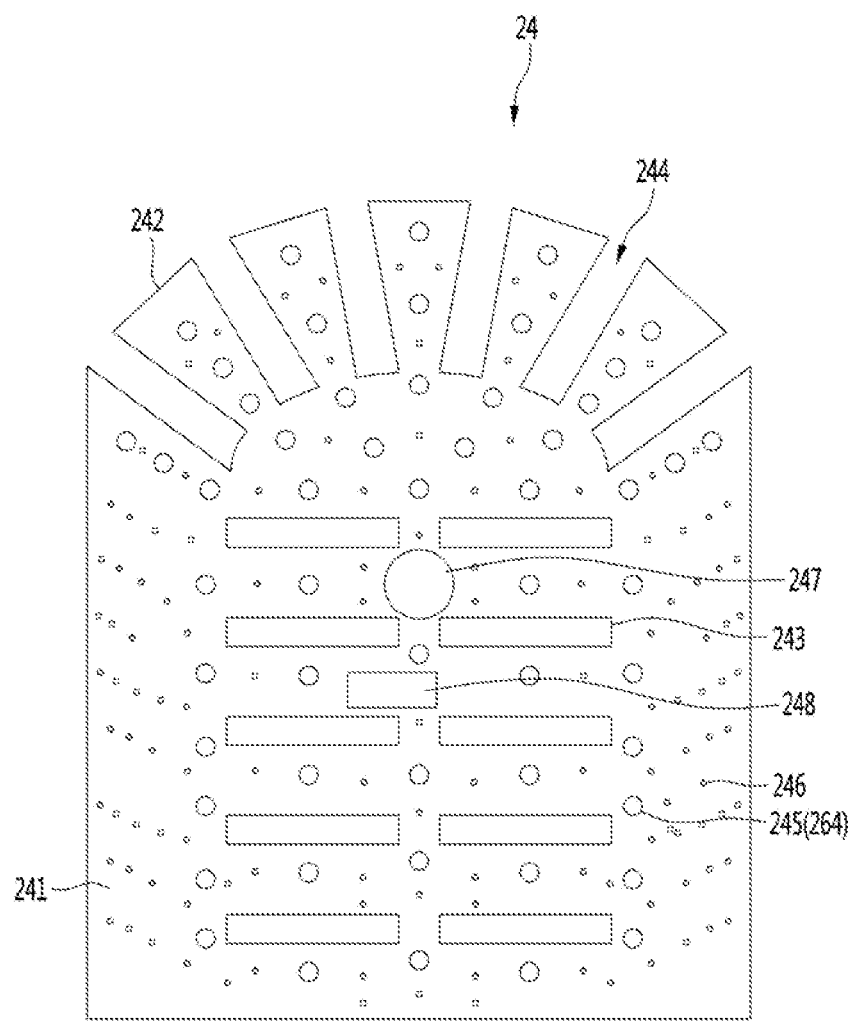

[Figure 6]
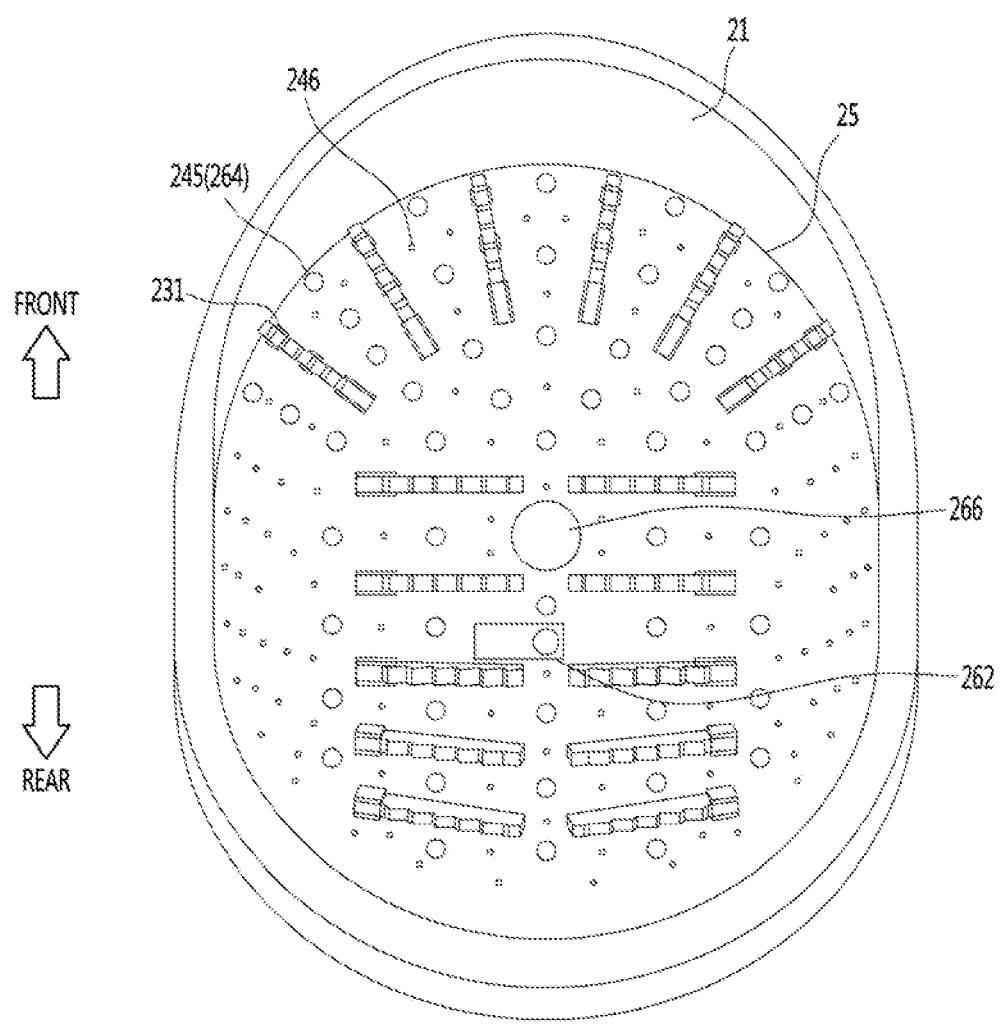

[Figure 7]
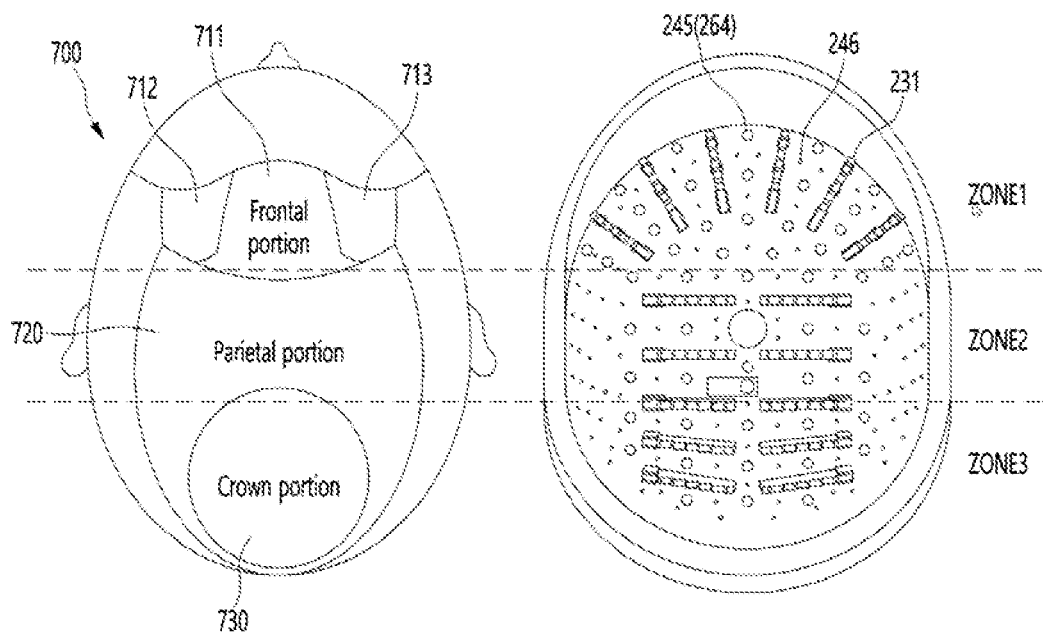
[Figure 8]
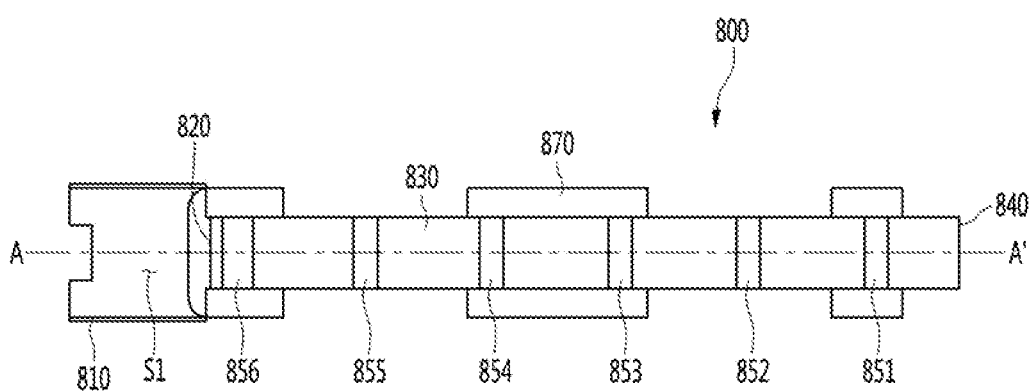

【Figure 9】
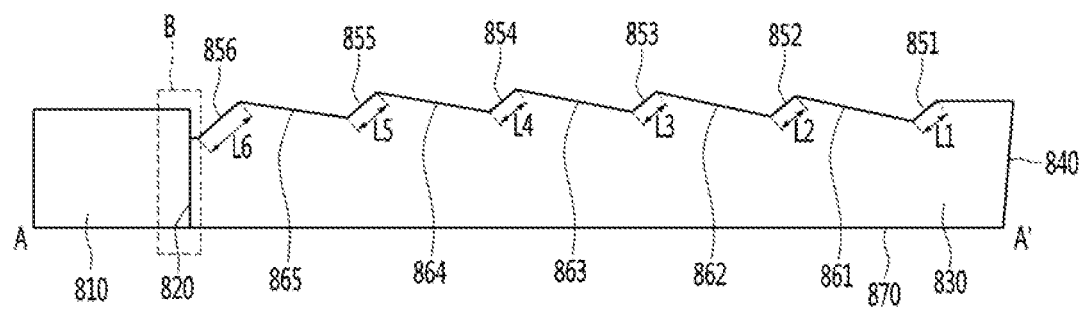
【Figure 10】
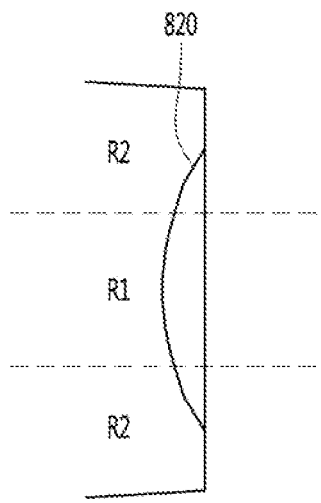

【Figure 11】
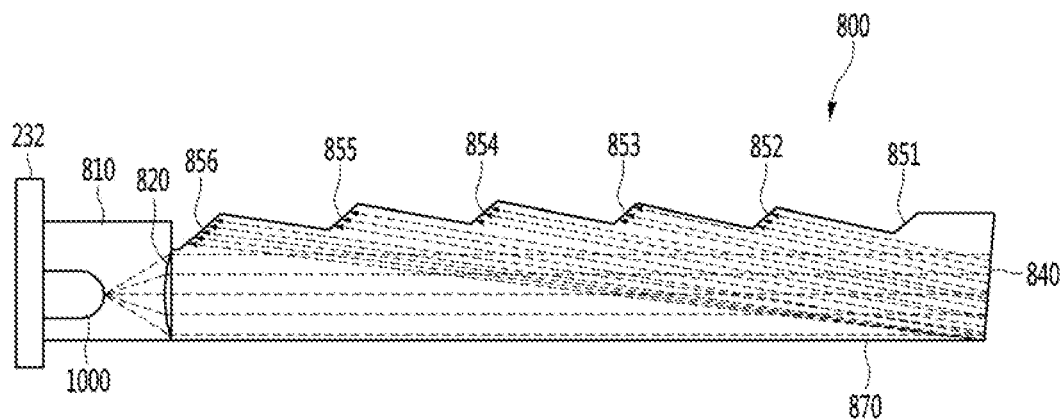
【Figure 12】
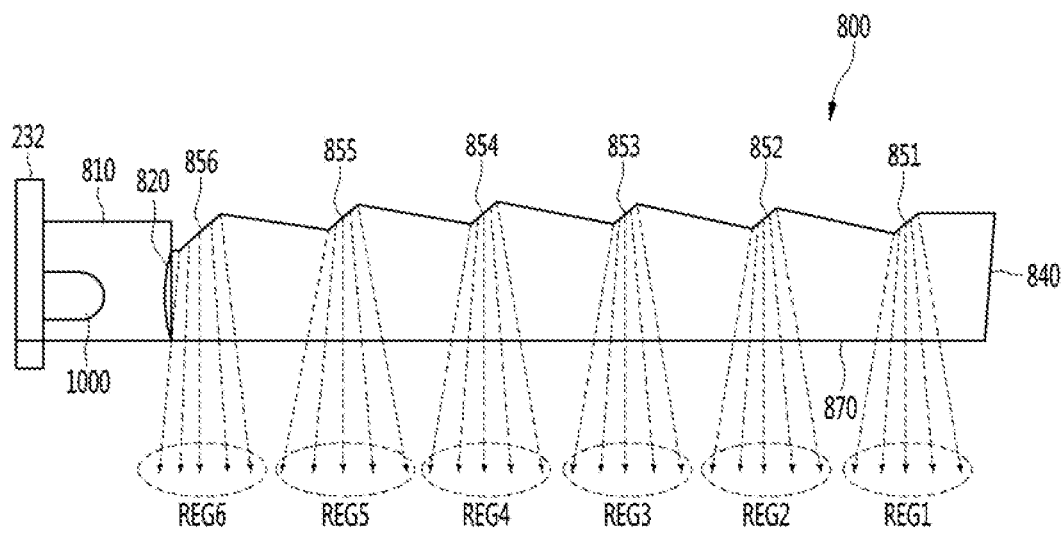

【Figure 13】
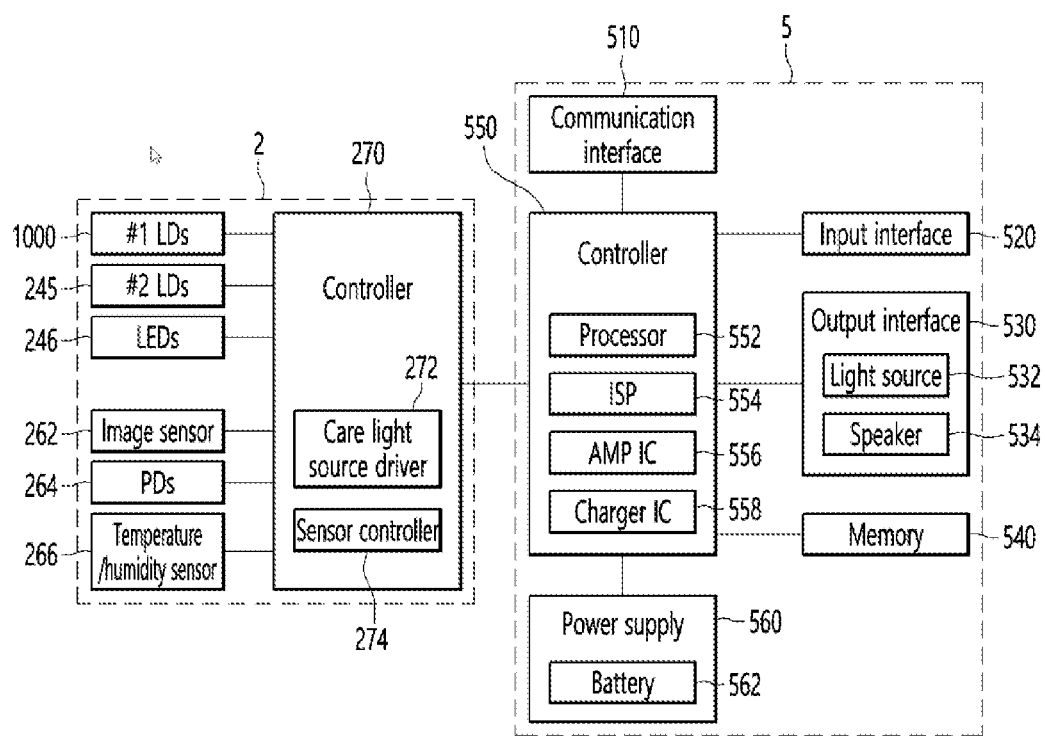

LIGHT OUTPUTTING DEVICE FOR SCALP CARE

CROSS-REFERENCE TO RELATED APPLICATIONS

This application is the National Phase of PCT International Application No. PCT/KR2019/006445 filed on May 29, 2019, which claims priority under 35 U.S.C. § 119 (e) to U.S. Provisional Application No. 62/746,566, filed on Oct. 17, 2018 and under 35 U.S.C. § 119 (a) to Patent Application No. 10-2019-0047475, filed in Republic of Korea on Apr. 23, 2019, all of these applications are hereby expressly incorporated by reference into the present application.

TECHNICAL FIELD

The present disclosure relates to a light outputting device, and more particularly, to a device that is worn on a user's head and outputs light for scalp care.

BACKGROUND ART

Modern people recognize their appearance as an important factor in notifying and expressing their appearance to others, and accordingly, are investing a lot of money and time in appearance management to overcome defects in appearance.

In particular, hair loss is caused by various causes such as environmental, genetic, mental, and physical causes, and various technologies or treatments for preventing or treating hair loss are being studied.

Low level laser therapy (LLLT) is a therapy that induces the promotion of metabolism in a corresponding area and activates the function of tissues by applying light of a specific wavelength to living tissues. Laser light used in low level laser therapy penetrates into living tissues and activates ions in cells to generate effects such as increased capillary production, increased oxygen concentration in blood, and stimulation of collagen production.

Based on such low level laser therapy, methods and devices for stimulating hair growth by applying laser light to a user's scalp to activate hair follicles and living tissues around the hair follicles have appeared.

DISCLOSURE

Technical Problem

An object of the present disclosure is to provide a light outputting device for scalp care having a structure that evenly applies laser light to a user's scalp while minimizing the number of laser light sources.

Another object of the present disclosure is to provide a light outputting device for scalp care having light source arrangement for maximizing hair loss treatment effects.

Still another object of the present disclosure is to provide a light outputting device for scalp care that controls light sources based on a user's hair loss type.

Technical Solution

According to an embodiment of the present disclosure, a light outputting device for scalp care includes a dome-shaped outer case defining an appearance, an inner case formed inside the outer case, and a plurality of light sources disposed in a space between the outer case and the inner case, wherein the plurality of light sources include a plurality of first laser light sources, and the optical outputting device includes a plurality of light guide mechanisms arranged corresponding to the plurality of first laser light sources to distribute laser light emitted from the first laser light sources apply the laser light toward the inner case.

Each of the plurality of light guide mechanisms may have a rod shape extending in a longitudinal direction, and be arranged to be directed at an angle closer to a tangent line at a position corresponding to the inner case in the longitudinal direction, than a vertical line with respect to the tangent line.

The plurality of first laser light sources may be arranged to be directed in the longitudinal direction of a corresponding light guide mechanism.

Each of the plurality of light guide mechanisms may include a laser light source accommodating portion having one end that is open and fastened to a laser light source mounting portion at the one end such that a corresponding first laser light source is accommodated therein; a light incident lens formed at the other end of the laser light source accommodating portion; and a guide body extending from the other end in the longitudinal direction, and the guide body may include a plurality of reflective surfaces.

The light incident lens may be convexly formed toward the first laser light source.

The light incident lens may be formed such that a curvature of a region including an edge is greater than a curvature of a region including a center.

The plurality of reflective surfaces may include a first reflective surface formed at an end of the guide body and at least one or more second reflective surfaces formed to be spaced apart from each other along one surface of the guide body.

The first reflective surface may be formed to be inclined at a predetermined angle to face the at least one second reflective surface.

The at least one or more second reflective surfaces may be formed to be inclined at a predetermined angle to face the first reflective surface.

The length of each of the at least one or more second reflective surfaces may be formed longer as a distance from the first reflective surface increases.

The guide body may further include at least one or more connection surfaces between the at least one or more second reflective surfaces, and the at least one or more connection surfaces may be formed to be inclined at a predetermined angle in a direction opposite to the at least one or more second reflective surfaces.

The guide body may further include a transmissive surface formed on a surface facing the one surface, and the transmissive surface may face the inner case.

The light outputting device may further include a care light source mounting portion disposed in a space between the outer case and the inner case, and the care light source mounting portion may be implemented with a flexible PCB (FPCB).

The plurality of light sources may further include a plurality of second laser light sources and a plurality of LEDs disposed on a surface facing the inner case among both surfaces of the care light source mounting portion.

The output of the first laser light source may be greater than an output of the second laser light sources, and the output of the second laser light sources may be greater than an output of the LEDs.

The number of the first laser light sources may be less than the number of the second laser light sources, and the number of the second laser light source may be less than a number of the LEDs.

The care light source mounting portion may further include openings respectively formed at positions corresponding to at least some of the plurality of light guide mechanisms.

The light outputting device may further include a support disposed between the outer case and the care light source mounting portion, and the support may include a fastening groove configured to fix the laser light source mounting portion to which the plurality of light guide mechanisms are fastened and a PCB fixing portion configured to fix the care light source mounting portion.

The inner case may be formed of any one of transparent polycarbonate, copolyester, or polymethyl methacrylate.

The inner case may include a plurality of light guide mechanism openings formed at positions respectively corresponding to the plurality of light guide mechanisms.

Advantageous Effects

According to the embodiments of the present disclosure, a light outputting device for scalp care includes a light guide mechanism that distributes laser light emitted from a laser light source and applies the laser light to a plurality of regions to evenly apply the laser light to various regions while minimizing the number of laser light sources, thereby maximizing the care effect.

In addition, as the number of laser light sources is minimized, excessive heat generation can be prevented and power consumption can be effectively reduced.

In addition, in the light outputting device for scalp care, laser light sources are arranged to correspond to regions where hair loss occurs mainly among the user's head regions, thereby maximizing an effect of preventing hair loss through scalp care.

DESCRIPTION OF DRAWINGS

FIG. 1 is a perspective view of a light therapy device for scalp treatment according to an embodiment of the present disclosure.

FIG. 2 is an exploded perspective view of a care body of the light outputting device shown in FIG. 1 as viewed from above.

FIG. 3 is an exploded perspective view of the care body of the light outputting device shown in FIG. 1 as viewed from below.

FIG. 4 is a view for describing a support portion included in the care body in more detail.

FIG. 5 is a bottom view of a care light source mounting portion included in the care body.

FIG. 6 is a bottom view of a care body of the light outputting device shown in FIG. 1.

FIG. 7 is a view for describing g a care body of the present disclosure having an arrangement shape of light sources based on a hair loss type.

FIG. 8 is a plan view of a light guide mechanism included in a care body.

FIG. 9 is a cross-sectional view of the light guide mechanism shown in FIG. 8 taken in the A-A' direction.

FIG. 10 is an enlarged view of a light incident lens of the light guide mechanism shown in FIG. 8.

FIGS. 11 to 12 are exemplary views for describing a state in which laser light is distributed and applied by the light guide mechanism according to an embodiment of the present disclosure.

FIG. 13 is a block diagram illustrating a control configuration of an light outputting device for scalp care according to an embodiment of the present disclosure.

MODE FOR INVENTION

Hereinafter, the embodiments disclosed herein will be described in detail with reference to the accompanying drawings, and the same or similar elements are designated with the same numeral references regardless of the numerals in the drawings and their redundant description will be omitted. The suffixes "module" and "unit or portion" for components used in the following description are merely provided only for facilitation of preparing this specification, and thus they are not granted a specific meaning or function. In addition, when it is determined that the detailed description of the related known technology may obscure the gist of embodiments disclosed herein in describing the embodiments, a detailed description thereof will be omitted. Further, the accompanying drawings are intended to facilitate understanding of the embodiments disclosed herein, and the technical spirit disclosed herein are not limited by the accompanying drawings. Therefore, the present disclosure should be construed as including all the changes, equivalents, and substitutions included in the spirit and scope of the present disclosure.

The terms coming with ordinal numbers such as 'first', 'second', or the like may be used to denote various components, but the components are not limited by the terms. The terms are used merely for the purpose to distinguish a component from the other component.

It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

As used herein, singular forms may include plural forms as well unless the context clearly indicates otherwise.

It will be further understood that the terms "comprises," "comprising," "having," "having," "includes," "including" and/or variations thereof, when used in this specification, specify the presence of stated features, integers, steps, operations, elements, and/or components, but do not preclude the presence or addition of one or more other features, integers, steps, operations, elements, components, and/or groups thereof.

Hereinafter, embodiments of the present disclosure will be described in detail with reference to the accompanying drawings.

FIG. 1 is a perspective view of a light outputting device for scalp treatment according to an embodiment of the present disclosure.

Referring to FIG. 1, a light outputting device 1 for scalp care (hereinafter referred to as 'light outputting device') according to an embodiment of the present disclosure is worn on the user's head to output light toward the user's scalp. The light outputting device 1 may serve to stimulate hair growth by stimulating hair follicle cells, increasing capillary production, increasing oxygen concentration in blood, stimulating collagen production, and the like as the light outputting device 1 outputs light.

This light outputting device 1 may include a care body 2, a circumference adjustment part 4, and an operation device 5.

The care body 2 is formed in the form of a dome to correspond to the shape of a person's head, so that light can be evenly applied to the user's scalp.

In an embodiment, the care body 2 may be formed to have a front curvature higher than a rear curvature when viewed from the top in terms of similarity to the shape of the person's head, but this is not necessarily.

That is, as used herein, the term "dome" is a concept including not only a geometric dome itself, but also a shape similar to the dome. In the present specification, the shape similar to the dome may mean a shape in which the shape has an arcuate shape (or streamline shape) in all of the left-right direction and the front-rear direction.

The care body 2 may be provided with a plurality of light sources that output light for the user's scalp care. The plurality of light sources may include laser light sources (e.g., laser diodes) and LEDs that output laser light. For example, the plurality of light sources may emit red light having a wavelength of about 630 nm to 670 nm, but are not limited thereto and may emit red light or infrared light. Red light can stimulate hair growth through stimulation of hair follicle cells, etc.

Meanwhile, laser light emitted by the laser light source has a stronger intensity than the light emitted from the LEDs and may penetrate deeper into the skin, thereby providing a higher scalp care effect. Accordingly, the laser light source in the care body 2 is arranged to emit laser light to a region in which scalp care is more needed when a user wears it, thereby enabling intensive care for the region. A care light source part provided in the care body 2 will be described in more detail through the following drawings.

On the other hand, the care body 2 may further include various sensors, such as a sensor for measuring a user's scalp condition (temperature, humidity, or the like), at least one sensor for detecting a user's hair loss type, and a sensor for detecting whether or not the light outputting device is worn, or the like.

The circumference adjustment part 4 is formed at a lower end of the care body 2 and may contact the circumferential surface of the head of the user when worn by the user. The circumference adjustment part 4 may include a structure capable of enabling length adjustment to correspond to the circumferential surfaces of heads of various users. The care body 2 is stably worn on the user's head by the circumference adjustment part 4 to apply light to the scalp.

Meanwhile, the light outputting device 1 may further include the user operation device 5 connected to the care body 2. For example, the user operation device 5 may be wiredly connected through the care body 2, a cable 52, and the like, but this is not necessary, and may be wirelessly connected through a wireless communication method For example, the user operation device 5 may be formed in a cylindrical shape so that the user can easily hold and use it with his or her hand. The user operation device 5 may be provided with at least one button as an input interface for operating the light outputting device 1.

The user operation device 5 may provide an interface for turning on/off the power of the care body 2 or setting an operation mode of the care body 2 for use by the user. As the user operation device 5 is implemented as a separate configuration from the care body 2, the user may conveniently operate an operation of the care body 2 by using the user operation device 5 while wearing the care body 2.

In addition, the user operation device 5 may be provided with a battery that provides power for the operation of the light outputting device. As the battery is provided in the user operation device 5, the weight of the care body 2 can be minimized to minimize user discomfort. Control elements included in the user operation device 5 will be described later with reference to FIG. 13.

Hereinafter, embodiments related to the structure of the care body 2 and the arrangement of light sources will be described in more detail with reference to FIGS. 2 to 7.

FIG. 2 is an exploded perspective view of a care body of the light outputting device shown in FIG. 1 as viewed from above. FIG. 3 is an exploded perspective view of the care body of the light outputting device shown in FIG. 1 as viewed from below. FIG. 4 is a view for describing a support portion included in the care body in more detail. FIG. 5 is a bottom view of a care light source mounting portion included in the care body.

Referring to FIGS. 2 to 3, a care body 2 may include an outer case 21, a support 22, a light guide 23, a care light source mounting portion 24, and an inner case 25.

The outer case 21 may define the overall appearance of the care body 2. For example, the outer case 21 may be made of a material such as plastic or stainless use steel (SUS), and may protect internal components of the care body 2 from the outside. On the other hand, the outer case 21 is formed to be opaque to block the light emitted from laser light sources or LEDs positioned therein not to leak to the outside.

According to an embodiment, a side opening 212 and/or an upper opening 214 may be formed in the outer case 21. When the care body 2 is worn by a user, air may circulate through the side opening 212 and/or the upper opening 214 between the inside of the care body 2 (a space between the care body 2 and the user's head) and the outside of the care body 2. Accordingly, heat generated by the driving of the light sources of the care body 2 is effectively radiated to the outside to prevent deterioration of the performance of the light sources.

Referring to FIGS. 2 to 4, the support 22 may be provided under the outer case 21.

A support body 221, which defines the overall outer shape of the support 22, may be formed in an arcuate shape in all of a left-right direction and a front-rear direction corresponding to the shape of the outer case 21.

The support 22 may be fastened to the inner surface of the outer case 21, but it is not necessary. For example, when the support 22 is fastened to the inner surface of the outer case 21, at least one fastening groove 222 is formed in the support body 221, and at least one fastening protrusion corresponding to the fastening groove 222 may be formed in the inner surface of the outer case 21. Meanwhile, the at least one fastening groove 222 may function as an opening allowing air circulation between the inside and the outside of the care body 2.

Meanwhile, the support 22 may support and fix the light guide 23 and the care light source mounting portion 24 with respect to the outer case 21 and/or the inner case 25.

Referring to FIG. 4, at least one light guide fastening groove 223 may be formed in the support body 221. For example, the at least one light guide fastening groove 223 may be formed in the form of an opening in a portion of the support body 221. As the laser light source mounting portion 232 of the light guide 23 is inserted into the light guide fastening groove 223, the light guide 23 may be supported and fixed by the support 22.

In addition, a plurality of PCB fixing portions 224 may be formed on a lower surface of the support body 221.

For example, each of the plurality of PCB fixing portions 224 may form an accommodation space in which a plurality of insertion protrusions formed on the upper surface of the care light source mounting portion 24 are inserted and accommodated. When the plurality of insertion protrusions are formed in a circular or cylindrical shape, the PCB fixing portion 224 may be implemented as a circular ring-shaped protrusion as shown in FIG. 4. In this case, an outer diameter of the plurality of insertion protrusions is formed to be equal to or smaller than an inner diameter of the PCB fixing portion 224, so that the plurality of insertion protrusions may be accommodated and fixed in the accommodation space. The above embodiment is for convenience of description, and the shape of the plurality of PCB fixing portions 224 is not limited thereto, and the plurality of PCB fixing portions 224 may be implemented in various forms to fix and support the care light source mounting portion 24.

According to an embodiment, a temperature/humidity sensor fixing portion 225 and an image sensor fixing portion 226 may be further formed on the support body 221. The temperature/humidity sensor fixing portion 225 is formed to correspond to a part of an upper portion of the temperature/humidity sensor mounted on the care light source mounting portion 24 to fix and support a temperature/humidity sensor. The image sensor fixing portion 226 may be implemented as an opening through which the upper portion of an image sensor mounted on the care light source mounting portion 24 is fixed and supported by passing.

That is, the care light source mounting portion 24 may be fixed and supported on the support 22 by the PCB fixing portion 224, the temperature/humidity sensor fixing portion 225, and the image sensor fixing portion 226. Meanwhile, according to an embodiment, the support 22 may be provided with a fastening portion that is directly fastened to the care light source mounting portion 24 to fix and support the care light source mounting portion 24.

Referring to FIGS. 2 and 3 again, the light guide 23 and the care light source mounting portion 24 may be provided between the support 22 and the inner case 25.

The light guide 23 may include a plurality of light guide mechanisms 231 and a laser light source mounting portion 232 provided with first laser light sources corresponding to each of the plurality of light guide mechanisms 231.

Each of the plurality of light guide mechanisms 231 may allow laser light emitted from a corresponding first laser light source to be distributed and applied to a plurality of regions. The first laser light source may be disposed so as not to directly apply laser light in the direction of the user's head (or the direction of the inner case).

The light guide mechanism 231 is formed in a rod shape, and the first laser light source may emit laser light in the longitudinal direction of the light guide mechanism 231.

In particular, the light guide mechanism 231 may be arranged at an angle closer to a tangent line at a position corresponding to the inner case 25 in the longitudinal direction, than a vertical line with respect to the tangent line. For example, the light guide mechanism 231 may be arranged such that its longitudinal direction is parallel to the tangent line, but is not limited thereto.

The light guide mechanism 231 may reflect the laser light emitted from the first laser light source to apply the laser light in the direction of the user's head (or the direction of the inner case).

Details of the light guide mechanism 231 will be described in more detail later with reference to FIGS. 8 to 12.

The laser light source mounting portion 232 may include a plurality of PCBs on each of which at least one first laser light source is mounted. FIGS. 2 to 3 illustrate a laser light source mounting portion 232 including three PCBs, but the number of PCBs is not limited thereto. Meanwhile, the PCB may be implemented with a flexible flexible PCB (FPCB).

The light guide mechanism 231 may be fastened to the laser light source mounting portion 232. In particular, the light guide mechanism 231 may be fastened to correspond to the position of the first laser light source mounted on the laser light source mounting portion 232.

When the laser light source mounting portion 232 is inserted into the light guide fastening groove 223 of the support 22, the light guide 23 may be fixed and supported by the support 22.

A plurality of second laser light sources (laser diodes) and a plurality of LEDs are mounted on the care light source mounting portion 24, and a circuit pattern for supplying power to the plurality of second laser light sources and the plurality of LEDs is formed in the care light source mounting portion 24. For example, the plurality of second laser light sources and the plurality of LEDs may be arranged to emit light downward from the care light source mounting portion 24 (in the direction of the inner case 25).

In this regard, referring to FIG. 5, the care light source mounting portion 24 may include a substrate 241. The substrate 241 may be implemented with a flexible FPCB. Accordingly, the care light source mounting portion 24 may be bent in a dome shape (or arcuate shape) corresponding to the shape of the outer case 21 and the inner case 25. The care light source mounting portion 24 is fixed and supported by the support 22 described above, so that the bent state can be stably maintained.

Meanwhile, the substrate 241 may include a plurality of openings 243 respectively formed at positions corresponding to some of the plurality of light guide mechanisms 231. The area of the opening 243 may be equal to or larger than the area of the light guide mechanism 231. The light guide mechanism 231 may be disposed on the corresponding opening 243, or a portion including a lower surface thereof may pass through the opening 243 and be disposed under the substrate 241.

Accordingly, the laser light emitted from each of the plurality of light guide mechanisms 231 may be applied to the user's scalp through the opening 243 formed at a corresponding position.

Meanwhile, a plurality of branch substrates 242 may be formed in one side of the substrate 241. The plurality of branch substrates 242 may extend from the one side of the substrate 241. In FIG. 5, an example in which the plurality of branch substrates 242 extend radially from one side of the substrate 241 is illustrated, but is not limited thereto.

For example, the substrate 241 may have three sides in a rectangular shape, and the remaining side may include two straight portions and a curved portion formed between the two straight portions. The curved portion may be formed to be convex in the outer direction of the substrate 241. Each of the plurality of branch substrates 242 may extend from the curved portion.

The plurality of branch substrates 242 may be formed to be spaced apart from each other by a predetermined distance. Further, the branch substrates 242 located at the edges may be formed such that one edge (e.g., the straight portion) of the substrate is also spaced apart by a predetermined distance. Accordingly, a plurality of gap regions 244 may be formed between the plurality of branch substrates 242 and in the branch substrate 242 and the substrate 241 positioned at the edges. The plurality of gap regions 244 may be formed to correspond to the light guide mechanisms 231 disposed relatively in front among the plurality of light guide mechanisms 231. The light guide mechanism 231 may be disposed on the gap regions 244, or a portion including a lower surface thereof may pass through the gap regions 244 and be disposed under the substrate 241.

Accordingly, the laser light emitted from each of the light guide mechanisms 231 disposed in front may be applied to the user's scalp through the gap regions 244.

Meanwhile, a plurality of second laser light sources 245 and LEDs 246 may be disposed on the bottom surface of the substrate 241 to be spaced apart from each other.

The output of the second laser light source 245 may be lower than that of the first laser light source 1000 (see FIG. 11) provided in the light guide 23, but it is not necessary. Further, the output of the LEDs 246 may be lower than the output of each of the first laser light source 1000 and the second laser light source 245.

Meanwhile, the number of first laser light sources 1000 may be less than the number of second laser light sources 245, and the number of second laser light sources 245 may be less than the number of LEDs 246.

The laser light sources 1000 and 245, and the LED 246 may emit red light. For example, the red light may correspond to a wavelength of about 630 nm to 670 nm, but is not limited thereto. According to an embodiment, the laser light sources 1000 and 245 and the LED 246 may emit infrared light having a wavelength of about 780 nm to 1 mm.

Meanwhile, each of the second laser light sources 245 may be provided with a photodiode 264 for sensing an amount of light. The light outputting device 1 may accurately detect a user's hair loss state or hair loss type using the image sensor 262 and a plurality of photodiodes 264.

Further, a temperature/humidity sensor mounting area 247 in which a temperature/humidity sensor 266 (see FIG. 6) is mounted, and an image sensor mounting area 248 in which an image sensor 262 (see FIG. 6) is mounted may be formed in the substrate 241. For example, each of the temperature/humidity sensor mounting area 247 and the image sensor mounting area 248 is formed closer to the center of the substrate 241 than the edges of the substrate 241, so that the areas are located in the parietal portion of the user (or the crown of the head) when the care body 2 is worn by a user. Accordingly, the temperature/humidity sensor 266 may effectively detect heat or moisture generated from the user's head. In addition, the image sensor 262 may effectively obtain an image for detecting whether hair loss has occurred in the parietal portion or the crown of the head.

Meanwhile, a care light source driver that drives the plurality of laser light sources and the plurality of LEDs, and a sensor controller that controls the image sensor 262 and the temperature/humidity sensor 266 may be provided a separate PCB positioned inside or outside the care body 2. According to an embodiment, the care light source driver and the sensor controller may be implemented in the care light source mounting portion 24.

Referring to FIGS. 2 and 3, the inner case 25 may be formed on the innermost side of the care body 2. The support 22, the light guide 23, and the care light source mounting portion 24 described above may be accommodated between the outer case 21 and the inner case 25 to be protected from the outside.

The inner case 25 may have a dome shape corresponding to the shape of the outer case 21. The inner case 25 may be smaller in size than the outer case 21, but it is not necessary.

The inner case 25 is made of a material such as transparent plastic or silicon, so that the light emitted from the laser light sources and LEDs accommodated therein may pass through the inner case 25 and be applied to the scalp of the user.

According to an embodiment, a plurality of light guide mechanism openings 252 corresponding to positions of the plurality of light guide mechanisms 23 may be formed in the inner case 25. The laser light emitted through the light guide 23 may be applied to the user's scalp through the plurality of light guide openings 252.

In addition, in order to improve the sensing accuracy of the temperature/humidity sensor 266 and the image sensor 262, a temperature/humidity sensor opening 254 corresponding to the temperature/humidity sensor 266 and an image sensor opening 256 corresponding to the image sensor 262 may be further formed in the inner case 25.

Hereinafter, features related to the arrangement of the light sources in the care body will be described in more detail with reference to FIGS. 6 to 7.

FIG. 6 is a bottom view of a care body of the light outputting device shown in FIG. 1. FIG. 7 is a view for describing g a care body of the present disclosure having an arrangement shape of light sources based on a hair loss type.

Referring to FIGS. 6 and 7, hair loss of a person 700 may mainly occur in a frontal portion 711, anterior temporal portions 712 and 713, a parietal portion 720, and/or a crown portion 730.

Accordingly, according to an embodiment of the present disclosure, the plurality of light guide mechanisms 231 and the second laser light sources 245 that emit laser light may be arranged to correspond to the frontal portion 711, the anterior temporal portions 712 and 713, the parietal portion 720, and the crown portion 730 to provide a more intensive care function for the portions.

On the other hand, in general, since there is a relatively low probability of hair loss occurring in temporal regions, the optical guide mechanisms 231 and the second laser light sources 245 are not disposed at positions corresponding to the temporal regions to provide an efficient care function, but is not limited thereto.

As described above with reference to FIG. 5, each of the plurality of light guide mechanisms 231 is exposed to the bottom of the care body 2 through the opening 243 or the gap region 244 of the substrate 241 to apply laser light to the scalp of the user. In addition, the inner case 25 is formed with light guide mechanism openings 252 corresponding to the plurality of light guide mechanisms 231, so that when the laser light emitted from the light guide mechanisms 231 passes through the inner case 25, it is possible to prevent the intensity thereof from decreasing.

In particular, the light guide mechanism 231 is implemented to distribute the laser light emitted from the first laser light source 1000 and apply the laser light to a plurality of regions. The spacing between the plurality of regions are smaller than the spacing between the second laser light sources 245. Accordingly, the light guide mechanism 231 can more densely apply the laser light to a specific region thereby maximizing a care effect. In addition, the light guide mechanism 231 may apply laser light to a wide area using one first laser light source 1000, thus maximizing efficiency. The light guide mechanism 231 will be described in more detail later with reference to FIGS. 8 to 12.

Meanwhile, the light emitted from the second laser light sources 245 and the LEDs 246 may pass through the inner case 25 and be applied to the user's scalp.

The plurality of LEDs 246 are evenly distributed over various areas of the substrate 241 to provide an overall care function for various regions of the user's head.

To classify the general types of hair loss, there are M-type hair loss in which hair loss gradually progresses from the anterior temporal portions 712 and 713, V-type hair loss in which hair loss gradually progresses from the crown portion 730, F-type hair loss in which hair loss gradually progresses from the parietal portion 720, U-type hair loss in which hair loss multiply progresses from the frontal portion 711, the anterior temporal portions 712 and 713, the parietal portion 720, and the crown portion 730, or the like.

That is, a region requiring intensive care may vary according to the type of hair loss of the user.

Accordingly, the light outputting device 1 according to the embodiment of the present disclosure may divide the laser light sources 1000 and 245 and the LEDs 246 provided in the care body 2 into a plurality of zones (e.g., ZONE1, ZONE2, ZONE3).

The light outputting device 1 uses at least one image sensor 262 and photodiodes 264 to detect a user's hair loss type, and controls the laser light sources 1000 and 245 and/or the LEDs 246 included in at least one zone based on the detected hair loss type.

Although not shown, an image sensor (not shown) for to detecting a hair loss state of the user's the frontal portion may be further provided in the inner surface of the outer case 21. For example, the image sensor (not shown) may be disposed on the front side of the inner surface of the outer case 21 so as to face the frontal portion of the user when worn.

In this case, the light outputting device 1 may detect the hair loss type of the user using the image sensor 262 disposed to capture an image of the parietal portion 720 and the crown portion 730 and an image sensor 262 disposed on the inner surface of the outer case 21 to capture an image of the frontal portion.

For example, when the detected hair loss type is M-type hair loss, a controller 550 of the light outputting device 1 may turn on only laser light sources corresponding to a first zone ZONE1, and may not turn on laser light sources corresponding to a second zone ZONE2 and a third zone ZONE3. Similarly, the controller 550 may turn on only the LEDs corresponding to the first zone ZONE1, and may not turn on the LEDs corresponding to the remaining zones. However, according to an embodiment, in order to provide an overall care function for the entire scalp, the controller 550 may also turn on all of the LEDs regardless of the hair loss type.

Meanwhile, as the light sources 1000, 245, and 246 emit light, the light sources 1000, 245, and 246 may emit heat together with the light. In this case, the performance of the light sources 1000, 245, and 246 may be gradually deteriorated due to the heat.

In addition, sweat may be generated from the user's scalp due to the heat, and light emitted from the light sources 1000, 245, and 246 may be reflected by the sweat generated on the scalp, thereby deteriorating the care effect.

The controller 550 may obtain temperature and humidity information through the temperature/humidity sensor 266 while applying light to the scalp by controlling the light sources 1000, 245 and 246, and control the light sources 1000, 245, and 246 based on the obtained temperature and humidity information.

For example, when the obtained temperature or humidity is equal to or higher than a reference temperature or a reference humidity, the controller 550 may stop the light output from the light sources 1000, 245, and 246. The controller 550 may resume the light output of the light sources 1000, 245, and 246 when a predetermined time has lapsed after the light output or when a temperature or humidity obtained during the stop of the light output decreases below the predetermined temperature or the predetermined humidity. Accordingly, the light outputting device 1 may perform an efficient care operation based on a temperature and a humidity.

Hereinafter, the light guide mechanism included in the care body 2 will be described in more detail with reference to FIGS. 8 to 12.

FIG. 8 is a plan view of a light guide mechanism included in a care body. FIG. 9 is a cross-sectional view of the light guide mechanism shown in FIG. 8 taken in the A-A' direction. FIG. 10 is an enlarged view of a light incident lens of the light guide mechanism shown in FIG. 8. FIGS. 11 to 12 are exemplary views for describing a state in which laser light is distributed and applied by the light guide mechanism according to an embodiment of the present disclosure.

Referring to FIGS. 8 to 9, a light guide mechanism 800 may distribute laser light emitted from the first laser light source 1000 (see FIG. 11) and apply the laser light to a plurality of regions. The light guide mechanism 800 of FIG. 8 has the same configuration as the light guide mechanism 231 described above with reference to FIG. 2 and the like.

The light guide mechanism 800 may include a laser light source accommodating portion 810.

One end of the laser light source accommodating portion 810 may be fastened to the laser light source mounting portion 232. One end of the laser light source accommodating portion 810 may be open, and an accommodation space S1 may be formed therein. The laser light source accommodating portion 810 may be fastened to a position corresponding to the first laser light source 1000 mounted on the laser light source mounting portion 232. As the laser light source accommodating portion 810 is fastened to the laser light source mounting portion 232, the first laser light source 1000 may be accommodated in the accommodation space S1.

A light incident lens 820 may be formed at the other end of the laser light source accommodating portion 810. Laser light emitted from the first laser light source 1000 accommodated in the accommodation space S1 may pass through the light incident lens 820 and be applied to a guide body 830. As described above, the first laser light source 1000 may be disposed so as not to directly face the inner case 25.

Referring to FIGS. 10 to 11, the light incident lens 820 may converge laser light emitted from the first laser light source 1000 to allow the laser light to be applied to a first reflective surface 840 at the end of the guide body 830. To this end, the light incident lens 820 may be formed in the shape of a convex lens when viewed from the side of the first laser light source 1000.

On the other hand, the light incident lens 820 may be formed such that the laser light that has passed through the light incident lens 820 is prevented from being concentrated on a specific point of the first reflective surface 840 and is evenly applied to the first reflective surface 840. As an example, the light incident lens 820 may be formed such that a curvature R1 of a region including a center portion is smaller than a curvature R2 of a region adjacent to the edge.

The light guide mechanism 800 may include a guide body 830 formed at the other end of the laser light source accommodating portion 810.

The guide body 830 may be formed in the form of a long passage from the laser light source accommodating portion 810 to the first reflective surface 840. The laser light transmitted through the light incident lens 820 may be applied to the first reflective surface 840 along the passage.

The guide body 830 may be implemented as an injection-molded body having a material such as transparent polycarbonate (PC), copolyester (COPE), and polymethyl methacrylate (PMMA).

The laser light transmitted through the light incident lens 820 may be applied to the first reflective surface 840 formed at the end of the guide body 830.

As shown in FIG. 11, the first reflective surface 840 may reflect at least a part of the applied laser light. In some embodiments, a reflective film or paint for reflecting the laser light may be formed on the first reflective surface 840.

In particular, the first reflective surface 840 may reflect the applied laser light to at least one or more second reflective surfaces 851 to 856 formed on the guide body 830. To this end, as shown in FIG. 9, the first reflective surface 840 may be formed to be inclined at a predetermined angle so as to face the upper side of the guide body 830.

At least one or more second reflective surfaces 851 to 856 may be formed on the upper surface of the guide body 830. As shown in FIG. 12, each of the at least one or more second reflective surfaces 851 to 856 may reflect the laser light, reflected and applied from the first reflective surface 840, to a transmissive surface 870 defining a bottom surface of the guide body 830. To this end, each of the at least one or more second reflective surfaces 851 to 856 may be formed to be inclined at a predetermined angle toward the first reflective surface 840.

Although the guide body 830 on which six second reflective surfaces 851 to 856 are formed is illustrated in the present specification, this is for convenience of description, and the number of second reflective surfaces may be variously changed.

Each of the at least one or more second reflective surfaces 851 to 856 may be formed to be spaced apart from each other on the top surface of the guide body 830. In some embodiments, a reflective film or paint for reflecting laser light may be formed on each of the at least one or more second reflective surfaces 851 to 856.

On the other hand, in order to minimize the difference in the amount of light reflected by each of the at least one or more second reflective surfaces 851 to 856 to the transmissive surface 870, the lengths L1 to L6 of the at least one or more second reflective surfaces 851 to 856 may be different from one another. For example, when the lengths L1 to L6 of the at least one or more second reflective surfaces 851 to 856 are identical to each other, the amount of reflected light is larger as the second reflective surface is closer to the first reflective surface 840, thus leading to the variation in the amount of light.

Accordingly, the lengths L1 to L6 of the at least one or more second reflective surfaces 851 to 856 are formed to be longer as the second reflective surface is far from the first reflective surface 840, thus minimizing the variation in the amount of light. That is, in the embodiment of FIG. 9, the lengths L1 to L6 of the second reflective surfaces 851 to 856 may increase as it goes from the first length L1 to the sixth length L6.

In some embodiments, each of the at least one or more second reflective surfaces 851 to 856 is formed to have an irregular pattern to reflect the laser light to a wider variety of regions.

The at least one or more connection surfaces 861 to 865 may be formed between the at least one or more second reflective surfaces 851 to 856. The connection surfaces 861 to 865 are formed to be inclined in a direction opposite to the at least one or more second reflective surfaces 851 to 856 to minimize irradiation of the laser light reflected from the first reflective surface 840 to the connection surfaces 861 to 865.

The lengths of the at least one or more connection surfaces 861 to 865 may be identical to each other, but not limited thereto.

According to an embodiment of the present disclosure, the guide body 830 is formed to have the first reflective surface 840 and the second reflective surfaces 851 to 856, thereby uniformly distributing the laser light emitted from the first laser light source 1000. In particular, compared to a structure in which the laser light emitted from the first laser light source 1000 is directly reflected to the transmissive surface 870, the length in the vertical direction can be reduced, so that the overall size of the light guide mechanism 800 can be effectively reduced.

The laser light reflected from the second reflective surfaces 851 to 856 may pass through the transmissive surface 870 and be applied to the user's scalp.

Referring to FIG. 12, laser light transmitted through the transmissive surface 870 and applied to the user's scalp can be irradiated to a number of regions REG1 to REG6 corresponding to the number of the second reflective surfaces 851 to 856. Meanwhile, as described above, the lengths of the second reflective surfaces 851 to 856 is formed longer as the distance from the first reflective surface 840 increases to minimize the variation in the amount of laser light reflected from the second reflective surfaces 851 to 856.

That is, the light guide mechanism 800 may uniformly irradiate the laser light to a wider area by uniformly applying laser light emitted from one first laser light source 1000 to a plurality of regions.

In particular, as illustrated in FIG. 12, the regions REG1 to REG6 may be adjacent to each other. For example, in order to directly apply laser light to the regions REG1 to REG6 using a plurality of laser light sources, the spacings between the plurality of laser light sources disposed on the substrate 241 become too narrow, leading to difficult implementation. In addition, as the number of laser light sources disposed on the substrate 241 increases, problems such as an increase in power consumption and an increase in heat generation occur.

According to an embodiment of the present disclosure, the care body 2 includes the plurality of light guide mechanisms 800 in regions of the user's scalp that require intensive care to maximize the care effect and reduce the number of laser light sources, thus, significantly reducing power consumption and overall heat generation.

According to an embodiment, a separation guide portion 880 for separating the light guide mechanism 800 from a mold may be formed on a side surface of the guide body 830. In order to prevent the laser light from leaking out through the separation guide portion 880, the separation guide portion 880 is not continuously formed on the side surface of the guide body 830, and a plurality of separation guides are provided to be spaced apart from each other at predetermined intervals.

FIG. 13 is a block diagram illustrating a control configuration of an light outputting device for scalp care according to an embodiment of the present disclosure.

In FIG. 13, the description will be given under assumption that control components of the light outputting device 1 are distributed and provided in the care body 2 and the user operation device 5. However, according to the embodiment, all of the control components may be provided in the care body 2.

Referring to FIG. 13, the care body 2 of the light outputting device 1 may include a plurality of first laser light sources 1000, a plurality of second laser light sources 245, a plurality of LEDs 246, at least one image sensor 262, a temperature/humidity sensor 266, and a controller 270.

The plurality of first laser light sources 1000 and the second laser light sources 245 may be implemented with a laser diode that emits laser light. As described above, the amount of light (output) of the first laser light source 1000 may be greater than the amount of light of the second laser light source 245. In addition, the number of first laser light sources 1000 may be less than the number of second laser light sources 245.

The plurality of first laser light sources 1000 may be provided corresponding to the plurality of light guide mechanisms 800 as described above with reference to FIGS. 8 to 12. The plurality of first laser light sources 1000 may not be disposed to directly face the scalp when the light outputting device 1 is worn by a user.

The plurality of second laser light sources 245 may be mounted to be spaced apart from each other on the care light source mounting portion 24 as shown in FIGS. 5 to 7.

Meanwhile, the first laser light sources 1000 and the second laser light sources 245 are, as described above in FIG. 7, disposed to correspond to an area including the frontal portion 711, the anterior temporal portions 712 and 713, the parietal portion 720, and the crown portion 730.

The plurality of LEDs 246 are disposed in various areas of the substrate 241 to apply light to various regions of the user's scalp.

Meanwhile, each of the first laser light sources 1000, the second laser light sources 245, and the plurality of LEDs 246 may emit red light having a wavelength of about 630 nm to 670 nm. Red light can stimulate hair growth by stimulating the activity of hair follicles.

At least one image sensor 262 may obtain an image including the user's head area. The controller 550 may detect a user's hair loss status, hair loss type, and the like based on the obtained image. According to an embodiment, a photodiode 264 may be provided in each of the second laser light sources 245. In this case, the controller 550 may detect the hair loss status or the hair loss type using the at least one image sensor 262 and the photodiode 264.

The temperature/humidity sensor 266 may detect a temperature and humidity of a region adjacent to the user's scalp during operation of the light outputting device 1. The controller 550 may control the light output of the light sources 1000, 245, and 246 based on the detected temperature and humidity.

The controller 270 provided in the care body 2 may include a care light source driver 272 that controls on/off of the light sources 1000, 245, and 246 and a a sensor controller 274 that controls the operations of the sensors 262, 264, and 266.

When a control signal for each of the light sources 1000, 245, and 246 is received from the processor 552 of the controller 550, the care light source driver 272 may control light output of the light sources 1000, 245, and 246 based on the received control signals.

When a control signal for each of the sensors 262, 264, and 266 is received from the processor 552, the sensor controller 274 may also control the driving of the sensors 262, 264, and 266 based on the received control signal. The sensor controller 274 may transmit sensing data received from each of the sensors 262, 264, and 266 to the processor 552.

According to an embodiment, the care light source driver 272 and the sensor controller 274 may be embedded in the controller 550 or may be implemented integrally with the processor 552.

Meanwhile, the user operation device 5 of the light outputting device 1 may include a communication interface 510, an input interface 520, an output interface 530, a memory 540, a controller 550, and a power supply 560.

The communication interface 510 may include at least one communication module for connecting the light outputting device 1 to a user's mobile terminal (smart phone, tablet PC, or the like) or a server. For example, the at least one communication module may support a short-range wireless communication method such as Bluetooth or a wireless Internet method such as Wi-Fi.

For example, the controller 550 may transmit operation or state information of the light outputting device 1 to the user's mobile terminal through the communication interface 510. In addition, the controller 350 may transmit the user's scalp state information, hair loss status information, and/or hair loss type information to the user's mobile terminal through the communication interface 510. The scalp state information, the hair loss status information, and the hair loss type information may be information obtained based on the sensing data of the image sensor 262 and/or the plurality of photodiodes 264.

The input interface 520 may receive an input related to power on/off of the light outputting device 1, settings of an operation mode, and the like from a user. For example, the input interface 520 may include at least one button.

The output interface 530 may output information on a power state, an operation mode, a battery state, or the like of the light outputting device 1. For example, the output interface 530 may include at least one light source 532 and a speaker 534 that outputs the information in an acoustic form.

The memory 540 may include control data for controlling components included in the light outputting device 1 or data related to light output settings of the light sources 1000, 245, and 246 according to each of a plurality of operation modes.

In addition, the memory 540 may store data or algorithms for generating scalp state information, hair loss status information, and/or hair loss type information from sensing values provided from the image sensor 262 and/or the plurality of photodiodes 264.

Further, the memory 540 may store data or algorithms for controlling the light output of the light sources 1000, 245, and 246 based on temperature and humidity information provided from the temperature/humidity sensor 266.

The memory 540 may be understood as a concept encompassing at least one volatile memory (such as RAM) and at least one nonvolatile memory (such as ROM and Flash memory).

The controller 550 may control the overall operation of the light outputting device 1. The controller 550 may include at least one processor (or controller). Further, the controller 550 may include at least one CPU, an application processor (AP), a microcomputer, an integrated circuit (IC), an application specific integrated circuit (ASIC), or the like as hardware components.

For example, the controller 550 may include a processor (main processor) 552, an image signal processor (ISP) 554, an amplifier IC 556, a charger IC 558, and the like.

The processor 552 may correspond to a main processor that controls the overall operation of the light outputting device 1. For example, the processor 552 may set an operation mode of the light outputting device 1 based on an input received through the input interface 520, and control components included in the light outputting device 1 according to the set operation mode. In addition, the processor 552 may control the operations of the other components 554, 556, 558 included in the controller 550, and even the operations of the care light source driver 272 and the sensor controller 274 of the care body 2.

Meanwhile, the processor 552 may detect a hair loss status or a hair loss type of the user based on sensing values obtained from the image sensor 262 and/or the plurality of photodiodes 264. The processor 552 may control the light output of the light sources 1000, 245, and 246 corresponding to at least one of the plurality of zones ZONE1 to ZONE3 (see FIG. 7) based on the detected hair loss status or the hair loss type.

The ISP 554 may generate an image by processing the sensing value obtained from the image sensor 262. The generated image may include the user's scalp. The processor 552 may transmit the generated image to a user's terminal or the like through the communication interface 510.

The amplifier IC 556 may control sound output of a speaker 534 included in the output interface 530, and the charger IC 558 may control the charge or supply of power of the battery 562 of the power supply 560.

The power supply 560 may provide power required for the operation of the light outputting device 1 to each of the components. For example, the power supply 560 may include the battery 562. The power supply 560 includes a terminal for connection with an external power supply source, and may charge the battery 562 with power supplied from the outside through the terminal. The power supply 560 may supply power to components included in the care body 2 through a cable 52.

The above-disclosed subject matter is to be considered illustrative, and not restrictive, and the appended claims are intended to cover all such modifications, enhancements, and other embodiments, which fall within the true spirit and scope of the present invention.

Thus, the embodiment of the present invention is to be considered illustrative, and not restrictive, and the technical spirit of the present invention is not limited to the foregoing embodiment.

Therefore, the scope of the present invention is defined not by the detailed description of the invention but by the appended claims, and all differences within the scope will be construed as being included in the present invention.

The invention claimed is:

1. A light outputting device for scalp care, comprising:
an outer case having a dome-shape and defining an appearance of the light outputting device;
an inner case disposed inside the outer case;
a plurality of light sources disposed in a space between the outer case and the inner case,
wherein the plurality of light sources comprise a plurality of first laser light sources; and
a plurality of light guide portions arranged corresponding to the plurality of first laser light sources to distribute laser light emitted from the plurality of first laser light sources and apply the laser light toward the inner case,
wherein each of the plurality of light guide portions comprises:
a laser light source accommodating portion having one end that is open and fastened to a laser light source mounting portion at the one end so that a corresponding first laser light source among the plurality of first laser light sources is accommodated in the laser light source mounting portion;
a light incident lens disposed at an opposite end of the laser light source accommodating portion, the opposite end being opposite to the one end; and
a guide body extending from the opposite end of the laser light source accommodating portion in a longitudinal direction of a corresponding light guide portion, a passage formed in the guide body,
wherein the guide body comprises a plurality of reflective surfaces,
wherein the plurality of reflective surfaces comprise:
a first reflective surface disposed at an end of the guide body; and
one or more second reflective surfaces spaced apart from each other along one surface of the guide body,
wherein the passage is disposed in a lengthwise direction of the guide body from the laser light source accommodating portion to the first reflective surface,
wherein the one or more second reflective surfaces are formed to be inclined at a predetermined angle toward the first reflective surface,
wherein the light incident lens converges the laser light emitted from the first laser light source to allow the laser light to be applied to the first reflective surface,
wherein the laser light transmitted through the light incident lens is applied to the first reflective surface along the passage, and
wherein the first reflective surface reflects the laser light to the one or more second reflective surfaces.

2. The light outputting device of claim 1, wherein each of the plurality of light guide portions has a rod or bar shape extending in the longitudinal direction, and
the longitudinal direction of each of the plurality of light guide portions is arranged at an angle that is closer to a tangent line at a position corresponding to the inner case than a vertical line with respect to the tangent line.

3. The light outputting device of claim 2, wherein the plurality of first laser light sources are arranged to be directed in the longitudinal direction of the corresponding light guide portion among the plurality of light guide portions.

4. The light outputting device of claim 1, wherein the light incident lens has a convex shape bulging toward the corresponding first laser light source.

5. The light outputting device of claim 4, wherein a curvature of an edge region of the light incident lens is greater than a curvature of a center region of the light incident lens.

6. The light outputting device of claim 1, wherein the first reflective surface is inclined at a predetermined angle to face the one or more second reflective surfaces.

7. The light outputting device of claim 1, wherein the one or more second reflective surfaces are inclined at a predetermined angle to face the first reflective surface.

8. The light outputting device of claim 1, wherein a length of each of the one or more second reflective surfaces is longer as a distance away from the first reflective surface increases.

9. The light outputting device of claim 1, wherein the guide body further includes one or more connection surfaces disposed between the one or more second reflective surfaces, and
wherein the one or more connection surfaces are inclined at a predetermined angle in a direction opposite to inclined angles of the one or more second reflective surfaces.

10. The light outputting device of claim 1, wherein the guide body further includes a transmissive surface formed on a surface facing the one surface of the guide body, and wherein the transmissive surface faces the inner case.

11. The light outputting device of claim 1, further comprising:
a care light source mounting portion disposed in a space between the outer case and the inner case,
wherein the care light source mounting portion includes a flexible printed circuit board (FPCB).

12. The light outputting device of claim 11, wherein the plurality of light sources further include:
a plurality of second laser light sources disposed on the care light source mounting portion and facing toward the inner case; and
a plurality of light emitting diodes (LEDs) disposed on the care light source mounting portion and facing the inner case.

13. The light outputting device of claim 12, wherein an output of each of the plurality of first laser light sources is greater than an output of each of the plurality of second laser light sources, and
wherein the output of each of the plurality of second laser light sources is greater than an output of each of the plurality of LEDs.

14. The light outputting device of claim 12, wherein a number of the plurality of the first laser light sources is less than a number of the plurality of the second laser light sources, and
wherein the number of the plurality of the second laser light source is less than a number of the plurality of LEDs.

15. The light outputting device of claim 11, further comprising:
a support disposed between the outer case and the care light source mounting portion,
wherein the support includes:
a fastening groove configured to fix the laser light source mounting portion to which the plurality of light guide portions are fastened; and
a printed circuit board (PCB) fixing portion configured to fix the care light source mounting portion, and
wherein the care light source mounting portion further includes openings respectively formed at positions corresponding to at least some of the plurality of light guide portions.

16. The light outputting device of claim 1, wherein the inner case is formed of any one of transparent polycarbonate, copolyester, or polymethyl methacrylate.

17. The light outputting device of claim 1, wherein the inner case includes a plurality of light guide portion openings disposed at positions respectively corresponding to the plurality of light guide portions.

18. A light outputting device, comprising:
an outer case having a rounded shape;
an inner case having a rounded shape; and
a plurality of light sources disposed between the outer case and the inner case, the plurality of light sources including a plurality of laser light sources or a plurality of light emitting diodes (LEDs); and
a light guide disposed between the outer case and the inner case, the light guide including a plurality of light guide portions arranged corresponding to one or more of the plurality of light sources configured to apply light toward the inner case,
wherein the light outputting device is configured to be worn by a user for scalp or skin care,
wherein each of the plurality of light guide portions comprises:
a laser light source accommodating portion having one end that is open and fastened to a laser light source mounting portion at the one end so that a corresponding first laser light source among the plurality of first laser light sources is accommodated in the laser light source mounting portion;
a light incident lens disposed at an opposite end of the laser light source accommodating portion, the opposite end being opposite to the one end; and
a guide body extending from the opposite end of the laser light source accommodating portion in a longitudinal direction of a corresponding light guide portion, a passage formed in the guide body,
wherein the guide body comprises a plurality of reflective surfaces,
wherein the plurality of reflective surfaces comprise:
a first reflective surface disposed at an end of the guide body; and
one or more second reflective surfaces spaced apart from each other along one surface of the guide body,
wherein the passage is disposed in a lengthwise direction of the guide body from the laser light source accommodating portion to the first reflective surface,
wherein the one or more second reflective surfaces are formed to be inclined at a predetermined angle toward the first reflective surface,
wherein the light incident lens converges the laser light emitted from the first laser light source to allow the laser light to be applied to the first reflective surface,
wherein the laser light transmitted through the light incident lens is applied to the first reflective surface along the passage, and
wherein the first reflective surface reflects the laser light to the one or more second reflective surfaces.

* * * * *